US00PP37114P2

(12) United States Plant Patent
Bourne

(10) Patent No.: US PP37,114 P2
(45) Date of Patent: Dec. 2, 2025

(54) GRAPEVINE NAMED 'SV33-82-49'

(50) Latin Name: *Vitis vinifera*
Varietal Denomination: SV33-82-49

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,550

(22) Filed: Apr. 14, 2025

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206
See application file for complete search history.

*Primary Examiner* — Susan Mccormick Ewoldt
(74) *Attorney, Agent, or Firm* — Eric C. Cole; Baker Manock & Jensen, PC.

(57) ABSTRACT

A new and distinct variety of grapevine plant named 'SV33-82-49' particularly characterized by its sweet, crisp black berries which ripen in mid-July in the McFarland, Calif. area.

5 Drawing Sheets

Latin name of the genus and species of the plant claimed: The plant claimed relates to a new and distinct variety of *Vitis vinifera*.

Variety denomination: The plant claimed shall be known as 'SV33-82-49'.

STATEMENT OF ANY FEDERALLY-SPONSORED RESEARCH AND DEVELOPMENT

The present invention is not subject to Federally-sponsored research or development.

BACKGROUND OF THE INVENTION

The present invention relates to a new and distinct cultivar of grapevine botanically known as *Vitis vinifera* L. and hereinafter referred to as grapevine named 'SV 33-82-49'. As used herein, 'grapevine' refers to all plant parts including vines, shoots, canes, tendrils, leaves, fruit and roots of 'SV33-82-49'. Grapevine named 'SV33-82-49' is the result of an effort to produce an early ripening, black, seedless table grape with fruit characteristics and productivity superior to currently available black, seedless cultivar 'Summer Royal' (unpatented). This new cultivar originated from a cross conducted in May 2012 near McFarland, Calif. between female parent grapevine selection 'SV17-50-583' (unpatented) and male parent grapevine selection 'SV21-66-226' (U.S. Plant Pat. No. 24,531). Resultant ovules from the cross were harvested 42 days after pollination and cultured on 'McCown's Woody Plant Medium'. Subsequently, the resultant embryonic plants were cultured in the same medium in the laboratory under twelve hours of light from standard fluorescent lamps at 29° C. The seedlings from this effort were transplanted to the greenhouse in October of 2012 and grown in the greenhouse at 29° C. with 12 hours illumination under high pressure sodium vapor lamps. The seedling population of 327 plants was planted in the field in the spring of 2013 near Delano, Calif. The new grapevine was selected from this seedling population on Aug. 21, 2015. It was then propagated by cuttings and grafted to 'Freedom' (unpatented) rootstock in 2016. The resultant vines were planted in a trial near McFarland, Calif. in May of 2016 and were trained to a t-trellis on 2.1 meter by 3 meter spacing. The present invention has been found to retain its distinctive characteristics through two successive asexual propagations.

Grapevine named 'SV33-82-49' differs from its female parent grapevine named 'SV17-50-583' (unpatented) in that 'SV33-82-49' has berries with small, soft seed traces less than 1 mm in length while 'SV17-50-583' has partially lignified seed traces about 3 mm in length.

Grapevine named 'SV33-82-49' differs from its male parent grapevine named 'SV21-66-226' (U.S. Plant Pat. No. 24,531) in that 'SV33-82-49' has black berries while 'SV21-6-226' produces berries which are green.

Grapevine named 'SV33-82-49' most closely resembles commercially available cultivar 'Autumn Royal' (unpatented) but differs from it in that grapevine 'SV33-82-49' produces clusters of fruit which ripen in mid-July while 'Autumn Royal' clusters ripen in late August in the Delano, California area.

SUMMARY OF THE INVENTION

The following are the most outstanding and distinguishing characteristics of the ripe fruit of this new variety when grown under normal horticultural practices near McFarland, California:

a. Berries with black skin.
b. Very firm berry texture and sweet, neutral flavor;
c. Berries which are responsive to gibberellic acid and trunk girdling applications.
d. Abundant, medium-sized bunches which ripen in mid-July in McFarland, California.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from plants about 5 years old grown near McFarland, Calif. in 2024.

DETAILED BOTANICAL DESCRIPTION

Figure 1:
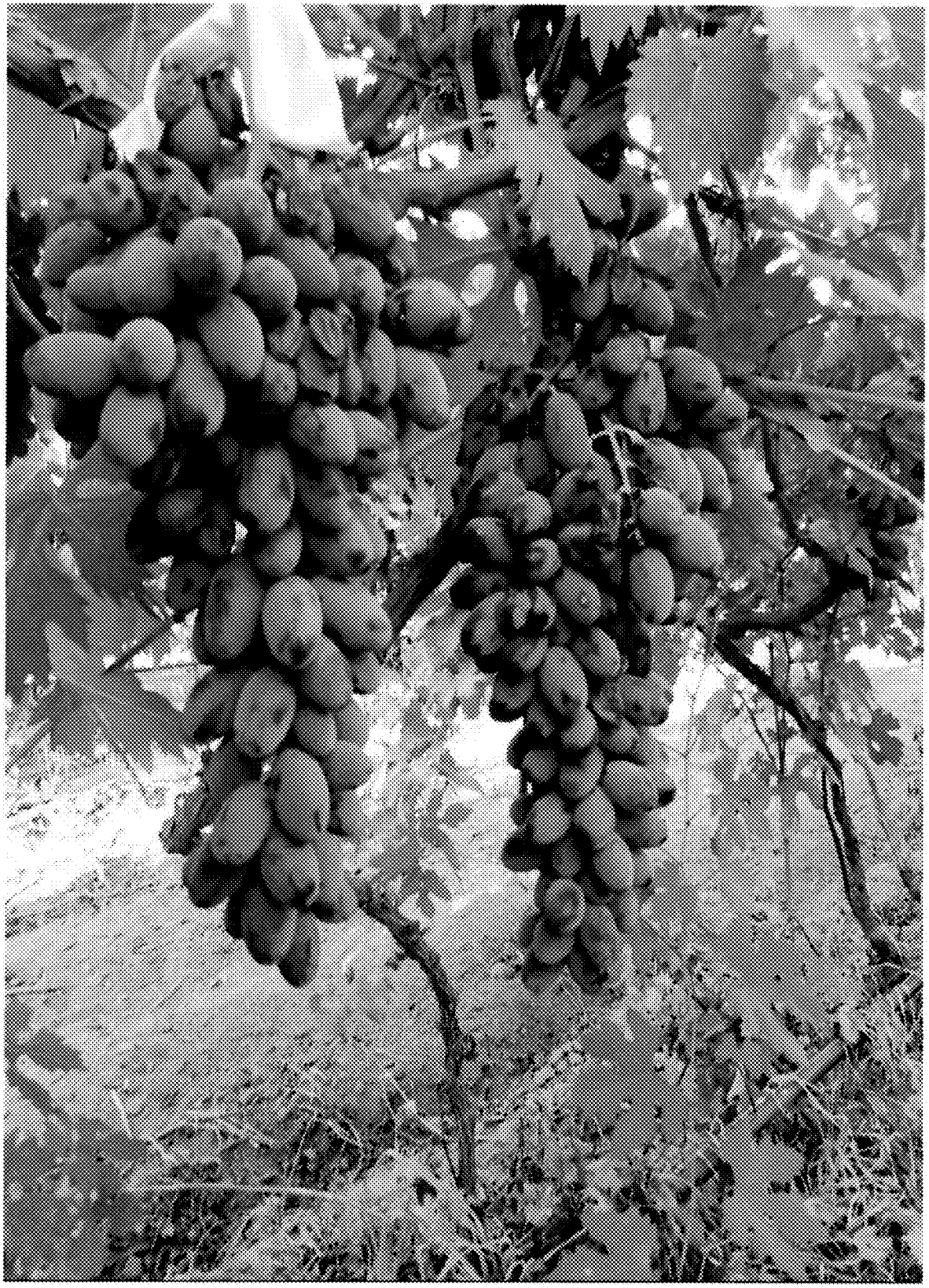
FIG. 1 Fruit clusters on seedling vine at time of selection.
Figure 2:
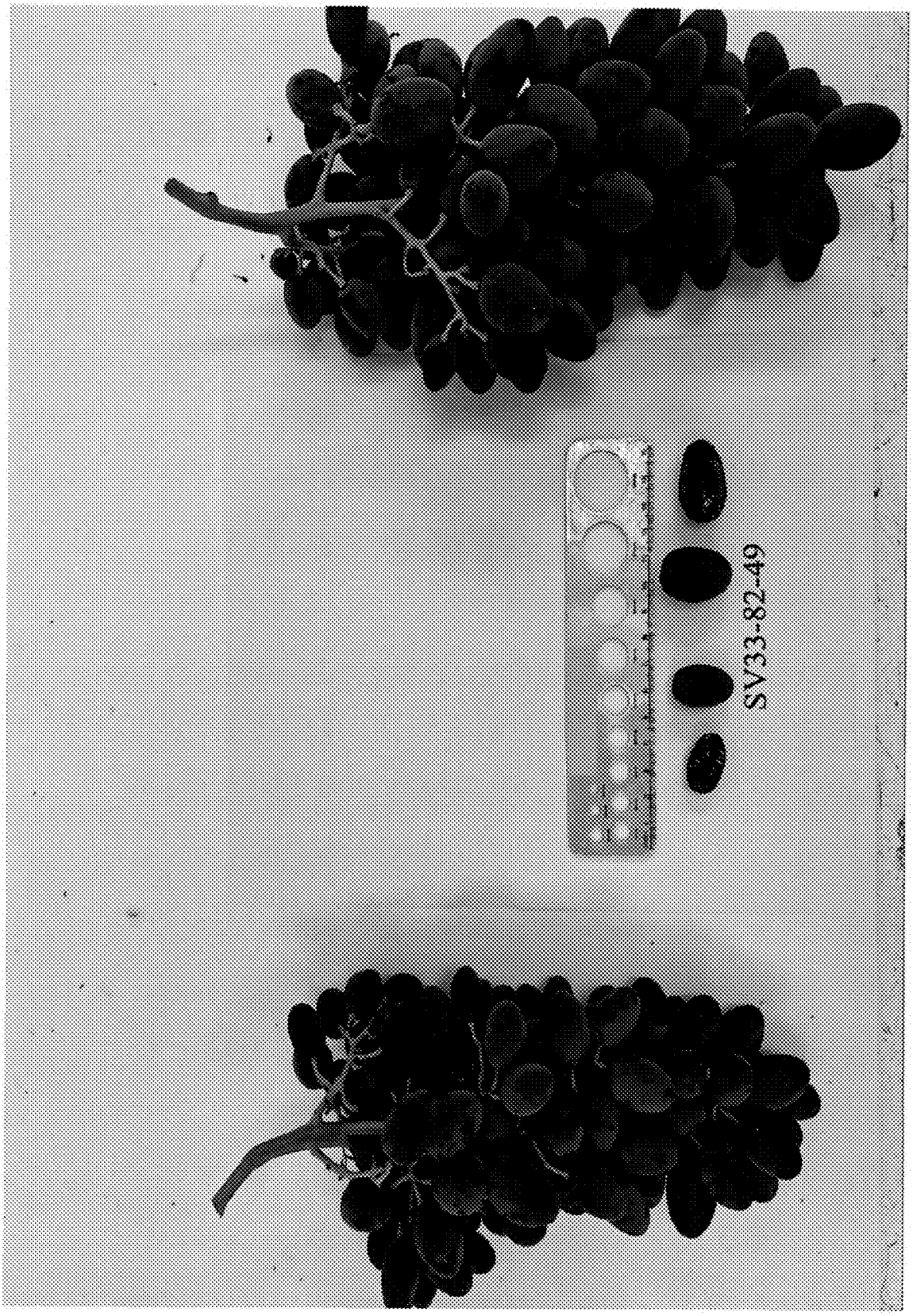
FIG. 2 A cluster and berries of natural fruit on the left. Cluster and berries from vines treated with exogenous gibberellic acid at flowering and 4 mm berry size plus trunk girdling on the right.
Figure 3:
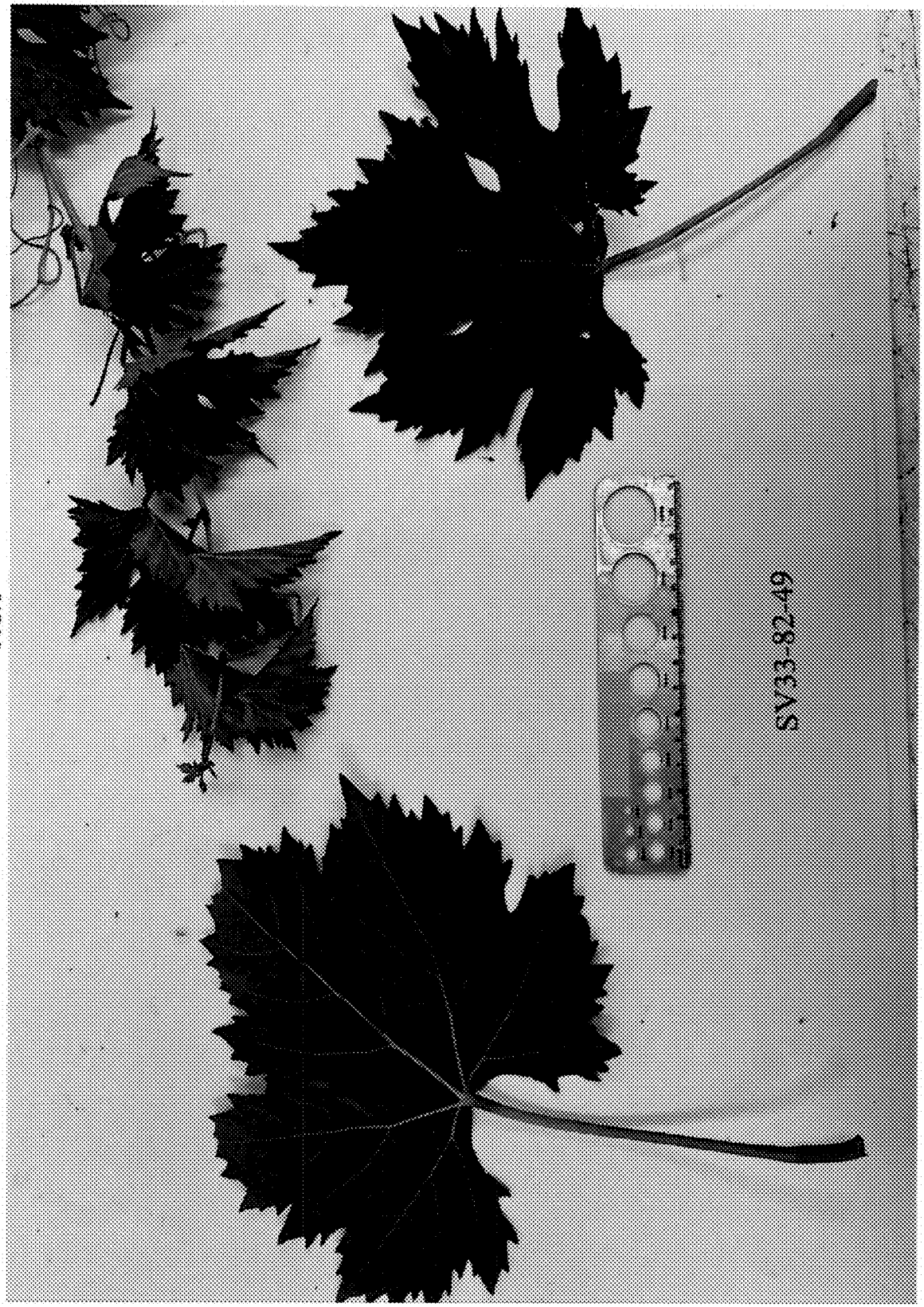
FIG. 3 Leaves, stems and tendrils.
Figure 4:
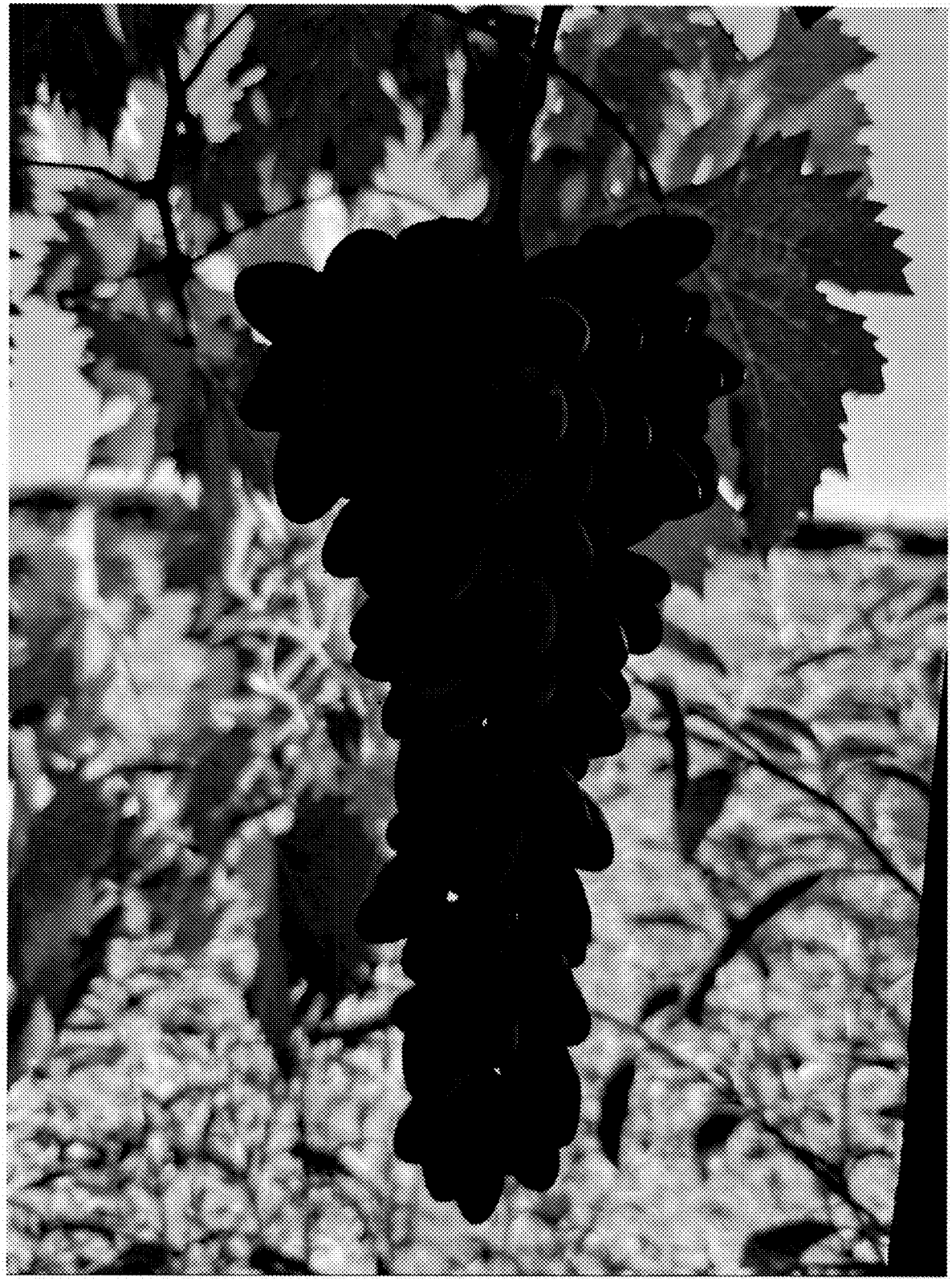
FIG. 4 Natural fruit cluster on mature vine.
Figure 5:
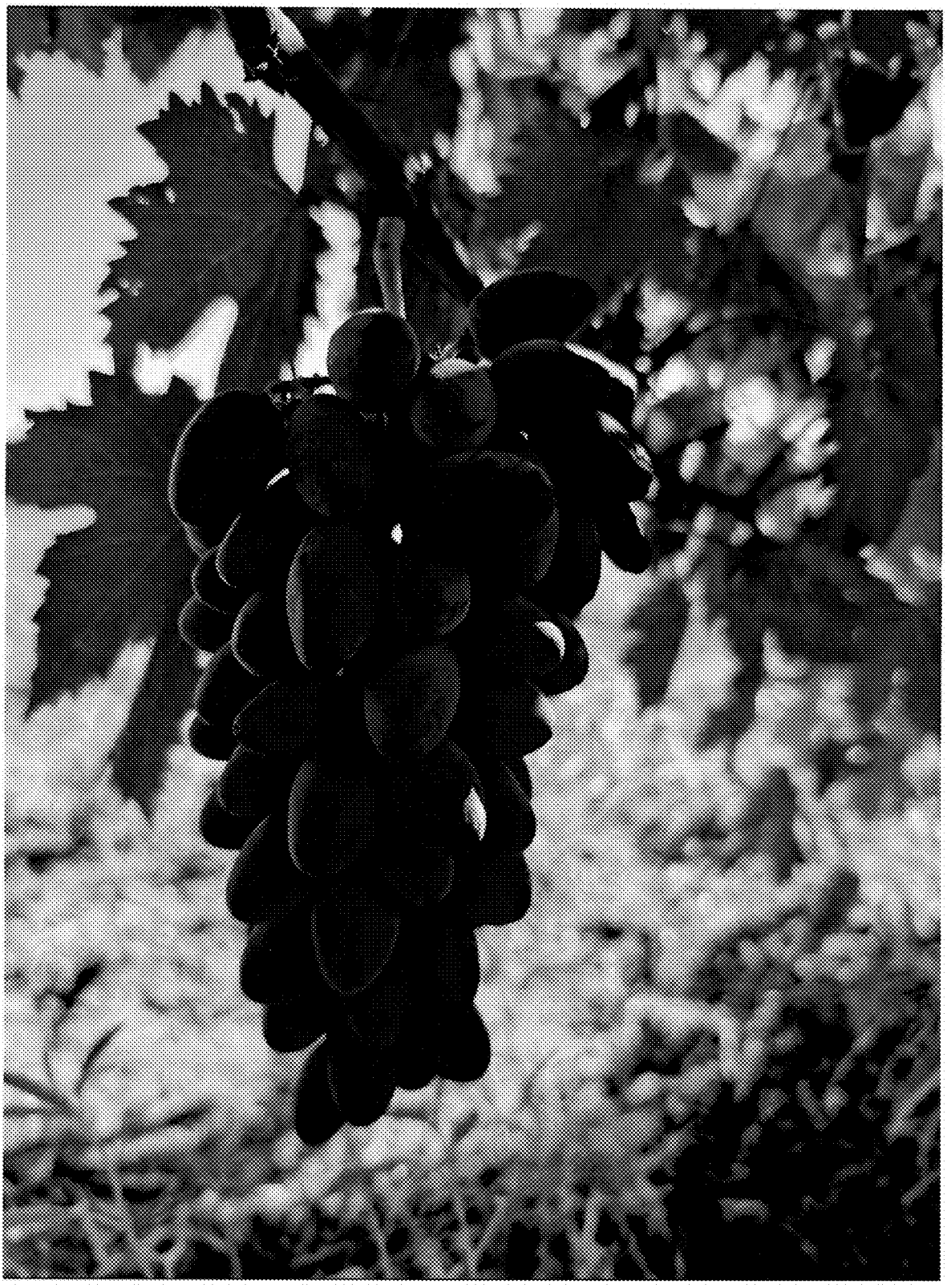
FIG. 5 Fruit cluster on vine treated with exogenous gibberellic acid and trunk girdling.

The following detailed description sets forth the distinctive characteristics of grapevine named 'SV33-82-49'. Descriptions of the new invention apply to vines of grapevine named 'SV33-82-49' grown on 'Freedom' (unpatented) rootstock at a density of 1,537 vines per hectare grown near McFarland, California in August 2023. These vines were in their sixth year of production having been planted in 2016. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV33-82-49'.

Plant:

*Vigor*.—Vines spur-pruned and shoot thinned to 32 shoots average 97.2 cm of growth per cane.

*Foliage*.—Medium, shoot growth is moderately vigorous with few lateral shoots.

*Productivity*.—High, up to 43,000 kg/ha.

*Hardiness*.—Observed to 0° C.

*Rootstock*.—'Freedom'.

Trunk:

*Shape*.—Broadly elliptical.

*Straps*.—Long, split.

*Surface texture*.—Shaggy, rough.

*Trunk circumference*.—22.7 cm.

*Inner bark color*.—RHS greyed-orange group 165A.

*Outer bark color*.—RHS brown group N200A.

Mature leaves:

*Average blade length*.—15.8 cm.

*Average blade width*.—18.6 cm.

*Size of blade*.—Medium.

*Shape*.—Pentagonal.

*Number of lobes*.—5.

*Anthocyanin coloration of main veins on the upper side of the blade*.—Absent.

*Mature leaf profile*.—Cupping around entire margin, undulating.

*Blistering* (*upper surface*).—Absent.

*Leaf blade tip*.—Curved upward.

*Margins*.—Lobed, doubly serrate.

*Apex*.—Broadly acuminate.

*Bases*.—Sagittate.

*Thickness*.—Thin.

*Undulation of blade between main and lateral veins*.—Slight cupping.

*Shape of teeth*.—Mixture of both sides straight and both sides convex.

*Length of teeth*.—8.2 mm.

*Width of teeth*.—8.6 mm.

*Ratio length/width of teeth*.—About 1:1.

*General shape of petiole sinus*.—Half open.

*Tooth at petiole sinus*.—Absent.

*Petiole sinus limited by veins*.—Absent.

*Shape of upper lateral sinus*.—Closed.

*Prostrate hairs between veins* (*lower surface*).—Absent.

*Erect hairs between veins* (*lower surface*).—Low density.

*Prostrate hairs on main veins* (*lower surface*).—Low density.

*Density of erect hairs on main veins* (*lower surface*).—Absent.

*Prostrate hairs on main veins* (*upper surface*).—Low density.

*Upper surface*.—Summer color: RHS green group 137A. Surface texture: Smooth. Surface appearance: Smooth. Goffering of blade: Absent.

*Lower surface*.—Summer color: RHS yellow-green group 146B. Anthocyanin coloration of main veins on lower leaf surface: Absent. Anthocyanin coloration on laterals: Absent. Glossiness: Low. Pubescence: Low density, prostrate. Surface texture: Rough. Surface appearance: Rough.

*Petiole*.—Length (cm): 13.0. Length of petiole compared to middle vein: About equal. Density of prostrate hairs: Absent. Density of erect hairs: Absent. Shape of base of petiole sinus: Sagittate. Color: In shade: RHS yellow-green group N144C. In sun: RHS yellow-green group N144C.

Tendrils:

*Number & pattern*.—Bifurcated and trifurcated; Continuous after 5th node.

*Length*.—16.9 cm.

*Diameter*.—3.0 mm.

*Texture*.—Smooth.

*Color*.—RHS yellow-green group N144D.

Growing tips (young shoot):

*Pubescence*.—High density, prostrate.

*Color*.—RHS yellow-green group 145A.

*Anthocyanins*.—Absent.

*Shape*.—Rounded.

*Apex*.—Fully open.

*Shoot attitude*.—Semi-erect.

Green summer shoots:

*Internode color upper surface*.—RHS yellow-green group 144B.

*Internode color lower surface*.—RHS yellow-green group 144A.

*Node color upper surface*.—RHS yellow-green group N144C.

*Node color lower surface*.—RHS yellow-green group N144C.

*Density of erect hairs on internodes*.—Absent.

Woody shoot:

*Canes*.—Shape: Broadly elliptical. Internode length: 8.9 cm. Internode diameter: 0.9 cm. Width at node: 1.5 cm. Main color: RHS Greyed-Orange group N167B.

*Buds*.—Shape: Conical. Bud fruitfulness: High. Full crop attained with spur pruning only. Length: 9.2 mm. Width: 7.7 mm. Height: 6.3 mm. Color: RHS Greyed-Orange group 177A. Texture: Smooth.

*Laterals*.—Number: 1 to 2 per cane. Length: 24.6 cm. Diameter: 5.3 mm. Internode length: 4.3 cm. Color: RHS yellow-green group 145A.

Flowers:

*Flower sex*.—Hermaphrodite.

*Position of first flowering nodes*.—3, 4, or 5.

*Number of inflorescences per shoot*.—1 or 2.

*Flower cluster width*.—4.1 cm.

*Flower cluster length*.—22.5 cm.

*Cluster stem color*.—RHS Yellow-Green group 145A, RHS Red-Purple group 60C.

*Calyptra color*.—RHS Yellow-Green group 146D.

*Ovary length*.—2 mm.

*Ovary width*.—1 mm.

*Ovary color*.—RHS Green group 143B.

*Filament length*.—2 mm.

*Filament color*.—RHS Yellow-Green group 145C.

*Anther length*.—1 mm.

*Anther color*.—RHS Yellow group 8B.

*Date of full bloom*.—May 5, 2024.

Fruit:

*Ripening period*.—Early mid-season, McFarland, California.

*Date of ripening*.—Jul. 15, 2024, McFarland, California.

*Use*.—Fresh market.

*Keeping quality*.—Very good.

*Shipping quality*.—Good.

*Solids-sugar*.—High, about 19 brix at full maturity.

*Refractometer test*.—20 brix, Jul. 15, 2024.

*Bunch*.—Size: Medium. Length (peduncle excluded): 25.0 cm. Width: 13.0 cm. Weight: Natural, without gibberellic acid treatment: 550 grams. With gibberellic acid treatment: 830 grams. Density: Well filled, high density. Number of berries: Natural, without gibberellic acid treatment: 113. With gibberellic acid treatment: 137. Form: Long conical.

*Peduncle*.—Length: 4.4 cm. Lignification: Absent. Color: RHS yellow-green group 146C.

*Berry*.—Size: Medium. Uniformity of size: Uniform. Weight: Natural, without gibberellic acid treatment: 4.8 grams. With gibberellic acid treatment: 6.0 grams. Shape: Natural, without gibberellic acid treatment: Ovate. With gibberellic acid treatment: Oblong. Presence of seeds: Seedless; most berries develop one or two small, soft rudimentary seeds less than 1.0 mm in length. Cross section: Circular. Dimensions: Longitudinal axis (Control): 2.6 cm. Longitudinal axis (G & G): 3.0 cm. Horizontal axis (Control): 1.9 cm. Horizontal axis (G & G): 1.8 cm. Skin color (without bloom): RHS greyed-purple group N186A. Coloration of flesh: RHS greyed-green group 195A. Juiciness of flesh: Very juicy. Berry firmness: Medium. Particular flavor: None. Bloom (cuticular wax): Strong. Pedicel length: 0.93 cm. Berry separation from pedicel: Very easy.

*Skin*.—Thickness: Medium. Texture: Tender, crisp. Reticulation: Absent. Roughness: Absent. Tenacity: Tenacious to flesh. Tendency to crack: Resistant.

Having thus described and illustrated our new variety of grapevine, I claim:

1. A new and distinct variety of grapevine plant named 'SV33-82-49', substantially as illustrated and described herein.

* * * * *